United States Patent [19]

Bellina

[11] 4,010,199

[45] Mar. 1, 1977

[54] MITICIDAL DITHIOBIURETS

[75] Inventor: Russell F. Bellina, Wilmington, Del.

[73] Assignee: E. I. Du Pont de Nemours and Company, Wilmington, Del.

[22] Filed: Apr. 17, 1975

[21] Appl. No.: 568,903

Related U.S. Application Data

[62] Division of Ser. No. 358,394, May 8, 1973, Pat. No. 3,890,322.

[52] U.S. Cl. .................. 260/552 R; 260/247.1 T; 260/256.5 R; 260/429 R; 260/429 K; 260/429.9; 260/438.1; 260/501.1; 260/501.15; 260/501.17; 260/501.21; 424/287; 424/289; 424/294; 424/316; 424/322; 424/248.5

[51] Int. Cl.² .................. A01N 9/12; C07C 157/13; C07F 3/02; C07F 3/06

[58] Field of Search ............... 260/552 R, 552.5 C, 260/553 B, 501.1, 501.15, 501.17, 501.21, 429 K, 429 R, 429.9, 438.1, 247.1 T

[56] References Cited

UNITED STATES PATENTS

| | | | |
|---|---|---|---|
| 2,410,862 | 11/1946 | Bousquet et al. | 424/300 X |
| 2,704,244 | 3/1955 | Goodhue et al. | 260/552 R X |
| 3,166,564 | 1/1965 | Diveley | 260/247.1 H X |
| 3,686,244 | 8/1972 | Marks | 260/552 R X |
| 3,776,955 | 12/1973 | Zielinski | 260/552 SC |
| 3,787,490 | 1/1974 | Zielinski | 260/552 R |
| 3,799,960 | 3/1974 | Marks | 260/429.9 X |
| 3,950,366 | 4/1976 | Diveley | 260/429 K |

OTHER PUBLICATIONS

CA 52: 1239g (1958).
Borkovec et al., CA 75: 109156e (1971).
Oliver et al., CA 79: 133650q (1973).

*Primary Examiner*—Daniel E. Wyman
*Assistant Examiner*—Thomas A. Waltz

[57] ABSTRACT

Novel dithiobiurets of one of the following formulas:

$$\text{CH}_3\text{-N(CH}_3\text{)-C(=S)-NH-C(=S)-N(A,E)-N-R} \quad \text{Ia}$$

and $$\text{CH}_3\text{-N(CH}_3\text{)-C(=S)-NH-C(=S)-N(R}_1\text{)-G-N(R}_2\text{)(R}_3\text{)} \quad \text{Ib}$$

where $R$, $R_1$, and $R_2$, and $R_3$ are certain organic radicals, the ring $$-N(A,E)N-$$

contains 5-8 atoms, and

A, E, and G are alkylene, and salts of these dithiobiurets.

An exemplary compound:
1,1-dimethyl-2-thio-3-[(4-propylpiperazin-1-yl)-thiocarbonyl]urea

4 Claims, No Drawings

MITICIDAL DITHIOBIURETS

This is a division of application Ser. No. 358,394, filed May 8, 1973 now U.S. Pat. No. 3,890,322.

BACKGROUND OF THE INVENTION

Japanese patent application No. 43-54280/1968, published Mar. 25, 1971, as Japanese Pat. No. 46-11679/1971 discloses a class of dithiobiurets of the general formula

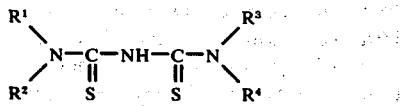

where $R^1$ and $R^2$ can be hydrogen or lower alkyl and $R^3$ and $R^4$ can be hydrogen, lower alkyl, cyanoalkyl, formyl, acetyl, halogen acetyl, and pyridyl. These compounds are said to be useful as insecticides, housefly antifertility agents, and mite-killing agents.

It has been found, however, that these compounds exhibit undesirable levels of phytotoxicity. It is this problem that the compounds of the present invention have overcome. Compounds of the present invention provide excellent protection against mites without causing any significant damage to the treated plants.

SUMMARY OF THE INVENTION

This invention is a class of novel miticidal compounds which can be represented by the following formulas:

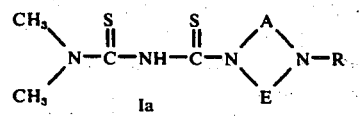

and

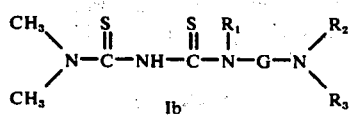

where
A is $-(CH_2)_a-$ or

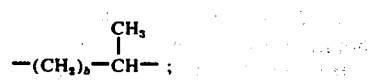

a is 0 through 4;
b is 1 or 2;
E is $-(CH_2)_d-$ or

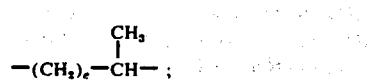

d is 2 through 5;
e is 1 or 2; with the provision that the total number of atoms in the ring

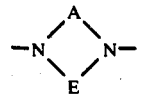

is between 5 and 8, inclusive;
R is alkyl of 1 through 6 carbon atoms; with the provision that the sum of carbon atoms in A, E, and R is not more than 10;
G is $-(CH_2)_m-$ or

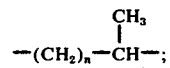

m is 0 through 6;
n is 1 or 2;
$R_1$ is methyl, $-(CH_2)_2-NR_2R_3$ or $-(CH_2)_3-NR_2R_3$;
$R_2$ is methyl or ethyl;
$R_3$ is alkyl of 1 through 6 carbon atoms;
$R_2$ and $R_3$ taken together can be $-(CH_2)_p-$; and
p is 4 through 6; with the provision that the sum of carbon atoms in G, $R_1$, $R_2$, and $R_3$ is not more than 10; and salts of the above compounds with acids or bases, the acids being selected from those having an ionization constant of at least $1 \times 10^{-7}$ and the salts formed with bases containing a cation selected from $Li^+$, $Na^+$, $K^+$, $Ca^{++}$, $Cu^{++}$, $Zn^{++}$, $Mg^{++}$, $Mn^{++}$, and

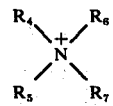

where
$R_4$, $R_5$, and $R_6$ can be the same or different and each can be hydrogen, alkyl of 1 through 4 carbon atoms, or hydroxy alkyl of 2 through 4 carbon atoms; and $R_7$ is hydrogen, alkyl of 1 through 12 carbon atoms, benzyl, amino, methylamino, or dimethylamino; $R_4$ and $R_5$ can be taken together to form a ring that is $-(CH_2)_1-O-(CH_2)_2-$ or $-(CH_2)_j-$ where j is 4-6 and $R_6$ and $R_7$ are H.

Examples of such acids include HCl, HBr, HF, HI, $H_2SO_4$, HSCN, $H_3PO_4$, $H_2SO_3$, acetic acid, oxalic acid, tartaric acid, benzoic acid, and N-lauryl-N-methyl-2-aminoethane sulfonic acid.

In addition to the miticidal utility of the compounds of the present invention, they may be used to prepare the class of compounds which comprise the subject matter of copending U.S. Patent Application Ser. No. 358,395, now U.S. Pat. No. 3,944,670 (Attorney's Docket No. B-8028-1) filed simultaneously herewith by Russell F. Bellina, which compounds are disclosed therein as being useful for the protection of plants from mites, fungi, aphids, Colorado potato beetle, Mexican bean beetle, and boll weevil.

For the sake of clarity it is mentioned that while the compounds of the present invention are, in fact, dithiobiurets and are identified generically as such, the various species within the scope of the present invention are identified as thiocarbonyl ureas and thiocarbamoyl ureas in order to permit the orderly and systematic naming of said species.

DETAILED DESCRIPTION OF THE INVENTION

Preferred Compounds

Certain of the compounds of Formulas Ia and Ib are preferred because of their ease of synthesis and higher activity. These compounds include those compounds of Formula Ia where:

A and E are -$(CH_2)_2$-; and
R is alkyl of 1 through 4 carbon atoms;
and salts thereof;
and those compounds of Formula Ib where:
G is -$(CH_2)_2$- or -$(CH_2)_3$-;
$R_1$ is methyl;
$R_2$ is methyl or ethyl;
$R_3$ is methyl or ethyl;
and salts thereof.

Compounds within this scope that are most preferred include:
1,1-dimethyl-2-thio-3-[(4-methylpiperazin-1-yl)-thiocarbonyl]urea
sodium salt of 1,1-dimethyl-2-thio-3-[(4-methylpiperazin-1-yl)-thiocarbonyl]urea
hydrobromic acid salt of 1,1-dimethyl-2-thio-3-[(4-methylpiperazin-1-yl)-thiocarbonyl]urea
1,1-dimethyl-2-thio-3-[(4-propylpiperazin-1-yl)-thiocarbonyl]urea
1,1-dimethyl-2-thio-3-[N-(2-dimethylaminoethyl)-N-methyl-thiocarbamoyl]urea
1,1-dimethyl-2-thio-3-[N-(3-dimethylaminopropyl)-N-methyl-thiocarbamoyl]urea
triethanolamine salt of 1,1-dimethyl-2-thio-3-[(4-methylpiperazin-1-yl)-thiocarbonyl]urea

Synthesis of the Compounds

The compounds of Formulas Ia and Ib can be prepared by the general procedure described in U.S. Pat. No. 3,166,564, by reacting an appropriate substituted thiocarbamoyl chloride with an alkali metal or ammonium thiocyanate to form the corresponding substituted thiocarbamoyl isothiocyanate and then reacting the latter with an appropriate secondary amine.

The salts of these compounds can be prepared by mixing an equimolar amount of the desired acid or an equimolar amount of the desired base with the appropriate dithiobiuret in a suitable solvent.

The following examples are given to illustrate the above-described processes. All parts are by weight unless specified otherwise.

EXAMPLE 1

Preparation of
1,1-dimethyl-2-thio-3-[(4-propylpiperazin-1-yl)-thiocarbonyl]urea A solution of 12 parts of N-propylpiperazine in 50 parts of acetone was added dropwise to a solution of 14.2 parts of dimethylthiocarbamoyl isothiocyanate in 100 parts of acetone at 10° to 15° C. The solution was then allowed to warm to room temperature, stirred for approximately two hours, and then filtered.

The solvent was removed under vacuum and the residue dissolved in 50 parts of 10% sodium hydroxide. The aqueous solution was washed twice with 50 parts of chloroform and then acidified with glacial acetic acid to about pH 7. The acidified solution was then extracted twice with 50-part portions of methylene chloride. The hydrocarbon layers were combined, dried over anhydrous magnesium sulfate, filtered, and the solvent was then removed under reduced pressure to give 13.5 parts of 1,1-dimethyl-2-thio-3-[(4-propyl-piperazin-1-yl)-thiocarbonyl]-urea as a viscous oil.

EXAMPLE 2

Preparation of
1,1-dimethyl-2-thio-3-[N-(2-dimethylaminoethyl)-N-methyl-thiocarbamoyl]urea A solution of 10.2 parts of N,N,N'-trimethyl ethylene diamine in 20 parts of acetone was added dropwise to 14.2 parts of dimethylthiocarbamoyl isothiocyanate in 100 parts of acetone at 10°–15° C. The solution was allowed to warm to room temperature, stirred for an additional 2 hours, and then filtered.

The solvent was removed under reduced pressure and the residue was dissolved in a mixture of 100 parts of chloroform and 50 parts of 10% aqueous sodium hydroxide solution. This mixture was shaken and then separated. The aqueous layer was acidified to about pH 7 with glacial acetic acid and then extracted three times with 50 part portions of methylene chloride. These extracts were combined, dried over anhydrous magnesium sulfate, filtered, and the solvent was removed therefrom under reduced pressure to give 13 parts of the crude product. Crystallization from ethanol gave 5 parts of pure 1,1-dimethyl-2-thio-3-[N-(2-dimethylaminoethyl)-N-methyl-thiocarbamoyl]urea, m.p. 93°–94° C.

EXAMPLE 3

Preparation of
1,1-dimethyl-2-thio-3-[N-(3-dimethylaminopropyl)-N-methyl-thiocarbamoyl]urea A solution of 11.6 parts of N,N,N'-trimethyl-trimethylenediamine in 30 parts of acetone was added dropwise to 14.2 parts of dimethylthiocarbamoyl isothiocyanate in 100 parts of acetone at 10°–15° C. The solution was allowed to warm to room temperature and then stirred for an additional hour.

The solvent was removed under reduced pressure and the residue was recrystallized twice from ethanol to give 3.2 parts of crystalline 1,1-dimethyl-2-thio-3-[N-(3-dimethylaminopropyl-N-methyl-thiocarbamoyl]urea, m.p. 108°–110° C.

EXAMPLE 4

Preparation of
1,1-dimethyl-2-thio-3-[(4-methylpiperazin-1-yl)-thiocarbonyl]urea A solution of 100 parts of N-methylpiperazine in 100 parts of acetone was added dropwise to 142 parts of dimethylthiocarbamoyl isothiocyanate in 650 parts of acetone at 10°–15° C. The resulting solution was allowed to warm to room temperature and stirred for 16 hours, during which time a solid precipitated. The solid material was filtered off to give 120 parts of 1,1-dimethyl-2-thio-3-[(4-methylpiperazin-1-yl)-thiocarbonyl]urea, m.p. 160° C. dec.

By using the appropriate amine, the following dithiobiurets can be prepared similarly:
1,1-dimethyl-2-thio-3-[(4-methyl-1,4-diazacyclohept-1-yl)-thiocarbonyl]urea
1,1-dimethyl-2-thio-3-[(4-pentyl-1,4-diazacyclohept-1-yl)-thiocarbonyl]urea
1,1-dimethyl-2-thio-3-[(2-methyl-1,2-diazacyclohept-1-yl)-thiocarbonyl]urea 1,1-dimethyl-2-thio-3-[(2-propyl-1,2-diazacyclopent-1-yl)-thiocarbonyl]urea
1,1-dimethyl-2-thio-3-[(2-hexyl-1,2-diazacyclohex-1-yl)-thiocarbonyl]urea
1,1-dimethyl-2-thio-3-[(2,3-dimethyl-1,2-diazacyclopent-1-yl)-thiocarbonyl]urea
1,1-dimethyl-2-thio-3-[(2-hexyl-3-methyl-1,2-diazacyclopent-1-yl)-thiocarbonyl]urea
1,1-dimethyl-2-thio-3-[(2,5-dimethyl-1,2-diazacyclopent-1-yl)-thiocarbonyl]urea
1,1-dimethyl-2-thio-3-[(3,4,5-trimethylpiperazin-1-yl)-thiocarbonyl]urea
1,1-dimethyl-2-thio-3-[(2,4,6-trimethylpiperazin-1-yl)-thiocarbonyl]urea
1,1-dimethyl-2-thio-3-[(2,4,5-trimethylpiperazin-1-yl)-thiocarbonyl]urea
1,1-dimethyl-2-thio-3-[(2,6-dimethyl-4-isopropylpiperazin-1-yl)-thiocarbonyl]urea
1,1-dimethyl-2-thio-3-[(3-methyl-1,3-diazacyclopent-1-yl)-thiocarbonyl]urea
1,1-dimethyl-2-thio-3-[(3-pentyl-1,3-diazacyclopent-1-yl)-thiocarbonyl]urea
1,1-dimethyl-2-thio-3-[(4-isopropylpiperazin-1-yl)-thiocarbonyl]urea
1,1-dimethyl-2-thio-3-[(4-sec-butylpiperazin-1-yl)-thiocarbonyl]urea
1,1-dimethyl-2-thio-3-[(4-ethylpiperazin-1-yl)-thiocarbonyl]urea
1,1-dimethyl-2-thio-3-[(1,2,2-trimethylhydrazino)-thiocarbonyl]urea
1,1-dimethyl-2-thio-3-[(1-methyl-2-ethyl-2-hexylhydrazino)-thiocarbonyl]urea
1,1-dimethyl-2-thio-3-[N-(azacyclohept-1-yl)-N-methyl-thiocarbamoyl]urea
1,1-dimethyl-2-thio-3-[N-(pyrrolidin-1-yl)-N-methyl-thiocarbamoyl]urea
1,1-dimethyl-2-thio-3-[1-(2-dimethylaminoethyl)-2,2-diethylhydrazino-thiocarbonyl]urea
1,1-dimethyl-2-thio-3-[1-(3-diethylaminopropyl)- 2,2-dimethylhydrazino-thiocarbonyl]urea
1,1-dimethyl-2-thio-3-[N-(pyrrolidin-1-yl)-N-(2-dimethylaminoethyl)-thiocarbamoyl]urea
1,1-dimethyl-2-thio-3-{N-(pyrrolidin-1-yl)-N-[2-(pyrrolidin-1-yl)ethyl]thiocarbamoyl}urea
1,1-dimethyl-2-thio-3-[N,N-bis(2-dimethylaminoethyl)thiocarbamoyl]urea
1,1-dimethyl-2-thio-3-[N-(6-dimethylaminohexyl)-N-methyl-thiocarbamoyl]urea
1,1-dimethyl-2-thio-3-[1-(2-diethylaminoethyl)-N-methyl-thiocarbamoyl]urea
1,1-dimethyl-2-thio-3-{N-[2-(pyrrolidin-1-yl)ethyl]-methyl-thiocarbamoyl}urea
1,1-dimethyl-2-thio-3-{N-[5-(pyrrolidin-1-yl)pentyl]-N-methyl-thiocarbamoyl}urea
1,1-dimethyl-2-thio-3-{N-[3-(N-ethyl-N-butylamino)-propyl-1]N-methyl-thiocarbamoyl}urea
1,1-dimethyl-2-thio-3-](5-methyl-1,5-diazacyclooct-1-yl)-thiocarbonyl]urea
1,1-dimethyl-2-thio-3-[(4-ethyl-1,4-diazacyclooct-1-yl)-thiocarbonyl]urea
1,1-dimethyl-2-thio-3-[(4,5,6-trimethyl-1,5-diazacyclooct-1-yl)-thiocarbonyl]urea
1,1-dimethyl-2-thio-3-[(2,8-dimethyl-5-ethyl-1,5-diazacyclooct-1-yl)-thiocarbonyl]urea
1,1-dimethyl-2-thio-3-[(4,5,8-trimethyl-1,5-diazacyclooct-1-yl)-thiocarbonyl]urea
1,1-dimethyl-2-thio-3-[N-(2-dimethylamino-1-methylethyl)-N-methyl-thiocarbamoyl]urea
1,1-dimethyl-2-thio-3-[N-(2-dimethylamino-2-methylethyl)-N-methyl-thiocarbamoyl]urea
1,1-dimethyl-2-thio-3-[N-(3-dimethylamino-1-methylpropyl)-N-methyl-thiocarbamoyl]urea
1,1-dimethyl-2-thio-3-[N-(3-dimethylamino-3-methylpropyl)-N-methyl-thiocarbamoyl]urea
1,1-dimethyl-2-thio-3-{N-[2-(pyrrolidin-1-yl)-1-methylethyl]-N-methyl-thiocarbamoyl}urea
1,1-dimethyl-2-thio-3-{N-[3-(azacyclohept-1-yl)-1-methylpropyl]-N-methyl-thiocarbamoyl}urea

EXAMPLE 5

Preparation of the nitric acid salt of 1,1-dimethyl-2-thio-3-[(4-methylpiperazin-1-yl)-thiocarbonyl]urea 1.5 Parts of concentrated nitric acid was added to a slurry of 5.0 parts of 1,1-dimethyl-2-thio-3-[(4-methylpiperazin-1-yl)-thiocarbonyl]urea (prepared as in the process described in Example 4 above) in 10 parts of water. The resulting mixture was stirred until all the compound was dissolved and the water was then evaporated under reduced pressure. The residue was crystallized from methanol to give 0.7 parts of the nitric acid salt of 1,1-dimethyl-2-thio-3-[(4-methylpiperazin-1-yl)-thiocarbonyl]urea, m.p. 150° C. dec.

By using the appropriate acid together with the appropriate dithiobiuret, the following acid salts can be prepared similarly:

hydrobromic acid salt of 1,1-dimethyl-2-thio-3-[(5-methyl-1,5-diazacyclooct-1-yl)-thiocarbonyl]urea
hydrobromic acid salt of 1,1-dimethyl-2-thio-3-[(4-ethyl-1,4-diazacyclooct-1-yl)-thiocarbonyl]urea
hydrochloric acid salt of 1,1-dimethyl-2-thio-3-[(4,5,6-trimethyl-1,5-diazacyclooct-1-yl)-thiocarbonyl]urea
hydrochloric acid salt of 1,1-dimethyl-2-thio-3-[(2,8-dimethyl-5-ethyl-1,5-diazacycloct-1-yl)-thiocarbonyl]urea
hydroiodic acid salt of 1,1-dimethyl-2-thio-3-[(4,5,8-trimethyl-1,5-diazacyclooct-1-yl)-thiocarbonyl]urea
hydroiodic acid salt of 1,1-dimethyl-2-thio-3-[N-(2-dimethylamino-1-methylethyl)-N-methyl-thiocarbamoyl]urea
sulfuric acid salt of 1,1-dimethyl-2-thio-3-[N-(2-dimethylamino-2-methylethyl)-N-methyl-thiocarbamoyl]urea
sulfuric acid salt of 1,1-dimethyl-2-thio-3-[N-(3-dimethylamino-1-methylpropyl)-N-methyl-thiocarbamoyl]urea
acetic acid salt of 1,1-dimethyl-2-thio-3-[N-(3-dimethylamino-3-methylpropyl)-N-methyl-thiocarbamoyl]urea
acetic acid salt of 1,1-dimethyl-2-thio-3-{N-[2-(pyrrolidin-1-yl)-1-methylethyl]-N-methyl-thiocarbamoyl}urea
nitric acid salt of 1,1-dimethyl-2-thio-3-{N-[3-(azacyclohept-1-yl)-1-methylpropyl]-N-methyl-thiocarbamoyl}urea

EXAMPLE 6

Preparation of the sodium salt of 1,1-dimethyl-2-thio-3-[(4-propylpiperazin-1-yl)-thiocarbonyl]urea 0.8 Part of sodium hydroxide is added to a solution of 5.5 parts of 1,1-dimethyl-2-thio-3-[(4-propylpiperazin-1-yl)-thiocarbonyl]urea in 50 parts of water. The resulting mixture can be stirred until all the solid is dissolved to give an aqueous solution of the desired sodium salt of 1,1-dimethyl-2-thio-3-[(4-propylpiperazin-1-yl)-thiocarbonyl]urea.

By using an appropriate base with an appropriate dithiobiuret, the following salts can be prepared similarly:

sodium salt of 1,1-dimethyl-2-thio-3-[(1,2,2-trimethylhydrazino)-thiocarbonyl]urea
sodium salt of 1,1-dimethyl-2-thio-3-[(1,2,2-trimethylhydrazino)-thiocarbonyl]urea
potassium salt of 1,1-dimethyl-2-thio-3-[(1-methyl-2-ethyl-3-hexylhydrazino)-thiocarbamoyl]urea
potassium salt of 1,1-dimethyl-2-thio-3-[N-(azacyclohept-1-yl)-N-methyl-thiocarbamoyl]urea
calcium salt of 1,1-dimethyl-2-thio-3-[N-(pyrrolidin-1-yl)-N-methyl-thiocarbamoyl]urea
calcium salt of 1,1-dimethyl-2-thio-3-[1-(2-dimethylaminoethyl)-2,2-diethylhydrazino-thiocarbonyl]urea
zinc salt of 1,1-dimethyl-2-thio-3-[1-(3-diethylaminopropyl)-2,2-dimethylhydrazino-thiocarbonyl]urea
zinc salt of 1,1-dimethyl-2-thio-3-[N-(pyrrolidin-1-yl)-N-(2-dimethylaminoethyl)-thiocarbamoyl]urea
magnesium salt of 1,1-dimethyl-2-thio-3-{N-(pyrrolidin-1-yl)-N-[2-(pyrrolidin-1-yl)-ethyl]-thiocarbamoyl}urea
magnesium salt of 1,1-dimethyl-2-thio-3-[N,N-bis(2-dimethylaminoethyl)-thiocarbamoyl]urea
manganese salt of 1,1-dimethyl-2-thio-3-[N-(6-dimethylaminohexyl)-N-methyl-thiocarbamoyl]urea
manganese salt of 1,1-dimethyl-2-thio-3-[1-(2-diethylaminoethyl)-N-methyl-carbamoyl]urea
copper salt of 1,1-dimethyl-2-thio-3-[N,N-bis(2-diethylamino)-thiocarbamoyl]urea
copper salt of 1,1-dimethyl-2-thio-3-{N-[2-(pyrrolidin-1-yl)ethyl]-N-methyl-carbamoyl}urea
tetramethyl ammonium salt of 1,1-dimethyl-2-thio-3-[(3,4,5-trimethylpiperazin-1-yl)-thiocarbonyl]urea
trimethyl-n-butyl ammonium salt of 1,1-dimethyl-2-thio-3-[2,4,6-trimethylpiperazin-1-yl)-thiocarbonyl]urea
tetra-n-butyl ammonium salt of 1,1-dimethyl-2-thio-3-[(2,4,5-trimethylpiperazin-1-yl)-thiocarbonyl]urea
trimethyl-n-dodecyl ammonium salt of 1,1-dimethyl-2-thio-3-[(2,6-dimethyl-4-isopropylpiperazin-1-yl)-thiocarbonyl]urea
tetraethyl ammonium salt of 1,1-dimethyl-2-thio-3-[(3-methyl-1,3-diazacyclopent-1-yl)-thiocarbonyl]urea
trimethyl benzyl ammonium salt of 1,1-dimethyl-2-thio-3-[(3-pentyl-1,3-diazacyclopent-1-yl)-thiocarbonyl]urea
tri-n-butyl benzyl ammonium salt of 1,1-dimethyl-2-thio-3-[(4-isopropylpiperazin-1-yl)-thiocarbonyl]urea
lithium salt of 1,1-dimethyl-2-thio-3-[(4-ethylpiperazin-1-yl)-thiocarbonyl]urea

EXAMPLE 7

Preparation of the triethanolamine salt of 1,1-dimethyl-2-thio-3-[(4-methylpiperazin-1-yl)-thiocarbonyl]urea Three parts of triethanolamine is added dropwise to a slurry of 5 parts of 1,1-dimethyl-2-thio-3-[(4-methylpiperazin-1-yl)-thiocarbonyl]urea in 40 parts of water at room temperature. The resulting slightly cloudy yellow solution is then filtered to remove impurities thereby affording 48 parts of a 17% aqueous solution of the triethanolamine salt of 1,1-dimethyl-2-thio-3-[(4-methylpiperazin-1-yl)-thiocarbonyl]urea.

Similarly, by use of the appropriate amine and dithiobiuret the following salts can be prepared:

ammonia salt of 1,1-dimethyl-2-thio-3-[(4-methylpiperazin-1-yl)-thiocarbonyl]urea
methylamine salt of 1,1-dimethyl-2-thio-3-[(4-ethylpiperazin-1-yl)-thiocarbonyl]urea
dibutylamine salt of 1,1-dimethyl-2-thio-3-[(4-propylpiperazin-1-yl)-thiocarbonyl]urea
dibutanolamine salt of 1,1-dimethyl-2-thio-3-[N-(2-dimethylaminoethyl)-N-methyl-thiocarbamoyl]urea
hydrazine salt of 1,1-dimethyl-2-thio-3-[N-(2-dimethylaminoethyl)-N-methyl-thiocarbamoyl]urea
N,N-dimethylhydrazine salt of 1,1-dimethyl-2-thio-3-[N-(2-dimethylaminopropyl)-N-methyl-thiocarbamoyl]urea
methylhydrazine salt of 1,1-dimethyl-2-thio-3-[N-(2-dimethylaminopropyl)-N-methyl-thiocarbamoyl]urea
morpholine salt of 1,1-dimethyl-2-thio-3-[(4-methylpiperazin-1-yl)-thiocarbonyl]urea
piperadine salt of 1,1-dimethyl-2-thio-3-[(4-methylpiperazin-1-yl)-thiocarbonyl]urea
hexamethyleneimine salt of 1,1-dimethyl-2-thio-3-[(4-methylpiperazin-1-yl)-thiocarbonyl]urea
dodecylamine salt of 1,1-dimethyl-2-thio-3-[N-(2-dimethylaminoethyl)-N-methyl-thiocarbamoyl]urea
pyrrolidine salt of 1,1-dimethyl-2-thio-3-[N-(2-dimethylaminoethyl)-N-methyl-thiocarbamoyl]urea
benzylamine salt of 1,1-dimethyl-2-thio-3-[N-(2-dimethylaminopropyl)-N-methyl-thiocarbamoyl]urea
trimethylamine salt of 1,1-dimethyl-2-thio-3-[N-(2-dimethylaminopropyl)-N-methyl-thiocarbamoyl]urea The use of the compounds of the present invention as miticides is the subject matter of copending U.S. patent application Ser. No. 358,396 (Attorney's Docket No. B-8048) filed May 8, 1973 by Colin L. McIntosh and now abandoned. A complete description of formulations and methods of application of these compounds is contained therein and is hereby incorporated herein by reference.

Use of the Compounds as Intermediates

The compounds of the present invention can be used as intermediates in the preparation of the corresponding dithiazolium salts. This reaction can be carried out under the general conditions described in U.S. Pat. No. 3,166,564 for oxidation of dithiobiurets in the presence of an acid to produce dithiazolium salts. These salts and their use as miticides, fungicides, and plant protectants are the subject matter of the above-mentioned copending U.S. patent application Ser. No. 358,395, filed May 8, 1973, (Attorney's Docket No. B-8028-1) now U.S. Pat. No. 3,944,670, which is a continuation-in-part of U.S. patent application Ser. No. 304,793, filed Nov. 8, 1972, now abandoned.

What is claimed is:
1. Compounds of the formula

$$CH_3\diagdown N-\overset{S}{\overset{\|}{C}}-NH-\overset{S}{\overset{\|}{C}}-\overset{R_1}{\overset{|}{N}}-G-N\diagup\overset{R_2}{\diagdown R_3}$$
$$CH_3\diagup \qquad\qquad\qquad\qquad Ib$$

G is —$(CH_2)_m$—or

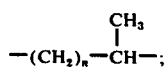

$m$ is 0 through 6;

$n$ is 1 or 2;

$R_1$ is methyl, $-(CH_2)_2-NR_2R_3$ or $-(CH_2)_3-NR_2R_3$;

$R_2$ is methyl or ethyl;

$R_3$ is alkyl of 1 through 6 carbon atoms;

with the provision that the sum of carbon atoms in G, $R_1$, $R_2$, and $R_3$ is not more than 10; and salts of these compounds with acids or bases, the acids being selected from those having an ionization constant of at least $1 \times 10^{-7}$ and the salts formed with bases containing the cation selected from $Li^+$, $Na^+$, $K^+$, $Ca^{++}$, $Cu^{++}$, $Zn^{++}$, $Mg^{++}$, $Mn^{++}$, and

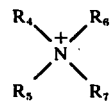

where $R_4$, $R_5$, and $R_6$ can be the same or different and each can be hydrogen, alkyl of 1 through 4 carbon atoms, or hydroxy alkyl of 2 through 4 carbon atoms; and $R_7$ is hydrogen, alkyl of 1 through 12 carbon atoms, benzyl, amino, methyl amino, or dimethylamino;

$R_4$ and $R_5$ can be taken together to form a ring that is $-(CH_2)_2-O-(CH_2)_2-$ or $-(CH_2)_j-$ where $j$ is 4–6 and $R_6$ and $R_7$ are H.

2. Compounds and salts thereof of claim 1 where G is $-(CH_2)_2-$ or $-(CH_2)_3-$;

$R_1$ is methyl;

$R_2$ is methyl or ethyl; and $R_3$ is methyl or ethyl.

3. Compound of claim 1 which is 1,1-dimethyl-2-thio-3-[N-(2-dimethylaminoethyl)-N-methyl-thiocarbamoyl]urea.

4. Compound of claim 1 which is 1,1-dimethyl-2-thio-3-[N-(3-dimethylaminopropyl)-N-methyl-thiocarbamoyl]urea.

* * * * *